United States Patent
Yoon

(10) Patent No.: US 7,385,207 B2
(45) Date of Patent: Jun. 10, 2008

(54) MOVABLE INCLINATION-ANGLE MEASURING APPARATUS FOR ION BEAM, AND METHOD OF USE

(75) Inventor: Young-Ha Yoon, Gyeonggi-do (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 204 days.

(21) Appl. No.: 11/115,848

(22) Filed: Apr. 26, 2005

(65) Prior Publication Data
US 2005/0247889 A1 Nov. 10, 2005

(30) Foreign Application Priority Data
May 7, 2004 (KR) ...................... 10-2004-0032198

(51) Int. Cl.
*H01J 37/317* (2006.01)
(52) U.S. Cl. .................................. 250/492.21; 250/397
(58) Field of Classification Search ........... 250/492.21, 250/397, 398
See application file for complete search history.

(56) References Cited

U.S. PATENT DOCUMENTS

| | | | |
|---|---|---|---|
| 5,343,047 A | | 8/1994 | Ono et al. |
| 5,641,969 A | | 6/1997 | Cooke et al. |
| 6,677,598 B1 | * | 1/2004 | Benveniste ............. 250/492.21 |
| 6,723,998 B2 | * | 4/2004 | Bisson et al. ................ 250/397 |
| 6,828,572 B2 | * | 12/2004 | Reece et al. ........... 250/492.21 |
| 6,852,984 B2 | * | 2/2005 | Krueger ....................... 250/397 |
| 6,858,854 B2 | * | 2/2005 | Keum et al. ........... 250/492.21 |
| 6,903,348 B2 | * | 6/2005 | Jang et al. ............. 250/492.21 |
| 2003/0197132 A1 | | 10/2003 | Keum et al. |

FOREIGN PATENT DOCUMENTS

| | | |
|---|---|---|
| JP | 4-209523 | 7/1992 |
| JP | 6-131999 | 5/1994 |
| KR | 2003-0082823 | 10/2003 |

\* cited by examiner

*Primary Examiner*—Keit T. Nguyen
(74) *Attorney, Agent, or Firm*—Marger, Johnson & McCollom, P.C.

(57) ABSTRACT

There is provided a movable ion beam inclination-angle measuring apparatus that can measure the inclination angle of either a spot ion beam or a ribbon ion beam. The apparatus is provided in an X-axis direction from an ion supplying unit of an ion implantation device. The apparatus includes an ion current measuring unit which has an ion-beam receiving device for receiving the ion beam, and has an ion current measuring part for measuring an ion current induced by the received ion beam. The apparatus further includes an angle adjusting unit adapted to adjust a receiving angle of the ion beam receiving device about a Y-axis and/or Z-axis and a position adjusting unit adapted to move the ion-beam receiving device in a Z-axis direction. The inclination angle is calculated by an inclination-angle calculating unit using the variation of the measured ion current depending on the adjustment of the receiving angle of the ion beam.

13 Claims, 5 Drawing Sheets

MOVABLE INCLINATION-ANGLE MEASURING APPARATUS FOR ION BEAM, AND METHOD OF USE

BACKGROUND OF THE INVENTION

This application claims the priority of Korean Patent Application No.: 2004-32198, filed on May 7, 2004, in the Korean Intellectual Property Office, the disclosure of which is incorporated herein in its entirety by reference.

1. Field of the Invention

The present invention relates to an apparatus for manufacturing a semiconductor device, and more particularly, to an inclination-angle measuring apparatus for an ion beam.

2. Description of the Related Art

Ion implantation is a technique for ionizing and accelerating impurities in a form of an ion beam and then implanting an appropriate amount of the ionized impurities into a desired region of a semiconductor substrate, material film or the like. Ion implantation is a part of the semiconductor fabrication procedure that selectively implants high-pure impurities into the substrate. In ion implantation, the position and the implantation depth of implanted ions can be precisely controlled and has an excellent characteristic of reappearance in comparison with a thermal diffusion process. U.S. Pat. Nos.: 5,343,047 and 5,641,969 disclose examples of ion implantation apparatuses.

However, as semiconductor devices have become more highly integrated and designed for higher performance levels, implanting ions requires more precise control. That is, the number, the implantation region and the implantation depth of the implanted ions need to be more strictly controlled in order to fabricate the semiconductor devices with higher integration and higher performance. In order to achieve this control, precise control of the inclination angle of an ion beam as well as the intensity of the ion beam is required.

If the inclination angle of the ion beam is imprecise, a channeling effect can be generated, and a shadow effect can be generated due to an upper mask pattern. Therefore, the inclination angle of the ion beam should be precisely measured to prevent the channeling effect and the shadow effect, and to precisely control the number, the implantation region and the implantation depth of the implanted ion.

In order to measure the inclination angle of the ion beam, ion implanting equipment generally includes an inclination-angle measuring apparatus. U.S. patent application publication No. 20030197132A1 published on Oct. 23, 2003 and entitled "Apparatus and method for measuring inclination angle of ion beam" by Keum et al. (the "Keum application"), which is commonly owned by an assignee of the present invention, discloses several examples of ion beam inclination-angle measuring apparatuses and a method for measuring an inclination angle of the ion beam using the same. The Keum application is hereby incorporated by reference in its entirety for all purposes as if fully set forth herein.

In the Keum application, FIG. 4 illustrates a schematic view of a construction of a spot ion beam inclination-angle measuring apparatus. Additionally, in the Keum application, FIG. 10 illustrates a schematic view of a construction of a ribbon ion beam inclination-angle measuring apparatus. In the Keum application, a Faraday cup assembly of an ion current measuring unit is rotated up and down and/or left and right, while ion current induced by the ion beam received in the Faraday cup assembly is measured. Additionally, a rotation angle of the Faraday cup assembly, at which the maximum ion current is generated, is calculated on the basis of the measured current and its variation. The inclination angle of the ion beam can be obtained from the calculated rotation angle of the Faraday cup assembly.

However, the Faraday cup assembly in the Keum application has a different structure for measuring a spot ion beam and for measuring a ribbon ion beam. The inclination-angle measuring apparatus for the spot ion beam cannot be used for measuring the inclination angle of the ribbon ion beam generated by the ion implantation equipment.

Further, the Faraday cup assembly measuring the inclination angle in the Keum application includes a single or plurality of Faraday cups formed of graphite. A hole in the Faraday cup that receives the ion beam is limited by its sidewall structure. If the sidewall structure is cast or molded using graphite to fabricate a Faraday cup, the hole have a size of several millimeters (mm). For example, even if it is not impossible, it is considerably difficult to limit the hole by the sidewall structure to a length (or diameter) smaller than 1 mm. If the hole of Faraday cup is large in size, the detection resolution of the inclination angle of the spot ion beam has a predetermined limitation. The limitation of the detection resolution becomes an obstacle in precisely controlling the inclination angle of the ion beam.

Additionally, since the ion beam is increased in size and accordingly, a Faraday cup and its dependent hole are concurrently increased in size, the detection resolution of the inclination angle becomes worse. For example, in a process where a 300 mm wafer is used, a larger ion beam is required to improve productivity. If an inclination-angle measuring apparatus has the same structure as a conventional inclination-angle measuring apparatus and is larger in size, the detection resolution of the inclination angle deteriorates.

Additionally, the Faraday cup assembly of the ribbon ion beam inclination-angle measuring apparatus disclosed in the Keum application is constructed as an assembly of a plurality of Faraday cups. The plurality of Faraday cups is fixedly disposed along a horizontal axis by a length of the ribbon ion beam. Accordingly, the Faraday cups adjacent to one another have a predetermined interval therebetween. The interval is twice as much as a sidewall thickness of the Faraday cup. Accordingly, the conventional inclination-angle measuring apparatus has a drawback in that the ribbon ion beam has a blind region between adjacent Faraday cups in which the inclination angle cannot be measured.

SUMMARY OF THE INVENTION

The present invention provides an ion beam inclination-angle measuring apparatus for an ion beam and an inclination-angle measuring method using the apparatus. The inclination-angle measuring apparatus has a simple system construction, and an inclination angle of a spot ion beam and an inclination angle of a ribbon ion beam can be measured with the same apparatus. Detection resolution for an inclination angle of an ion beam is excellent, and the measurement of the ion beam does not have a blind region.

According to an aspect of the present invention, there is provided a movable ion beam inclination-angle measuring apparatus positioned in an X-axis direction from an ion supplying unit of an ion implantation device. The apparatus includes: an ion current measuring unit which has an ion-beam receiving device adapted to receive the ion beam, and has an ion current measuring part adapted to measure an ion current induced by the received ion beam; an angle adjusting unit adapted to adjust a receiving angle of the ion beam by the ion-beam receiving unit around a Y-axis and/or Z-axis; a position adjusting unit adapted to move the ion-beam receiving unit in the Z-axis direction; and an inclination-angle calculating unit adapted to calculate an inclination angle of the ion beam from the variation of the measured ion current depending on the adjustment of the receiving angle of the ion beam.

The ion-beam receiving device may include a Faraday cup assembly, which may include a Faraday cup body having a plurality of holes which are arrayed in horizontal and vertical directions. The Faraday cup body may be comprised of a single structure and the diameter of each of the plurality of holes is in the range of about five micrometers to less than about 1 mm.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION

Figure 1:
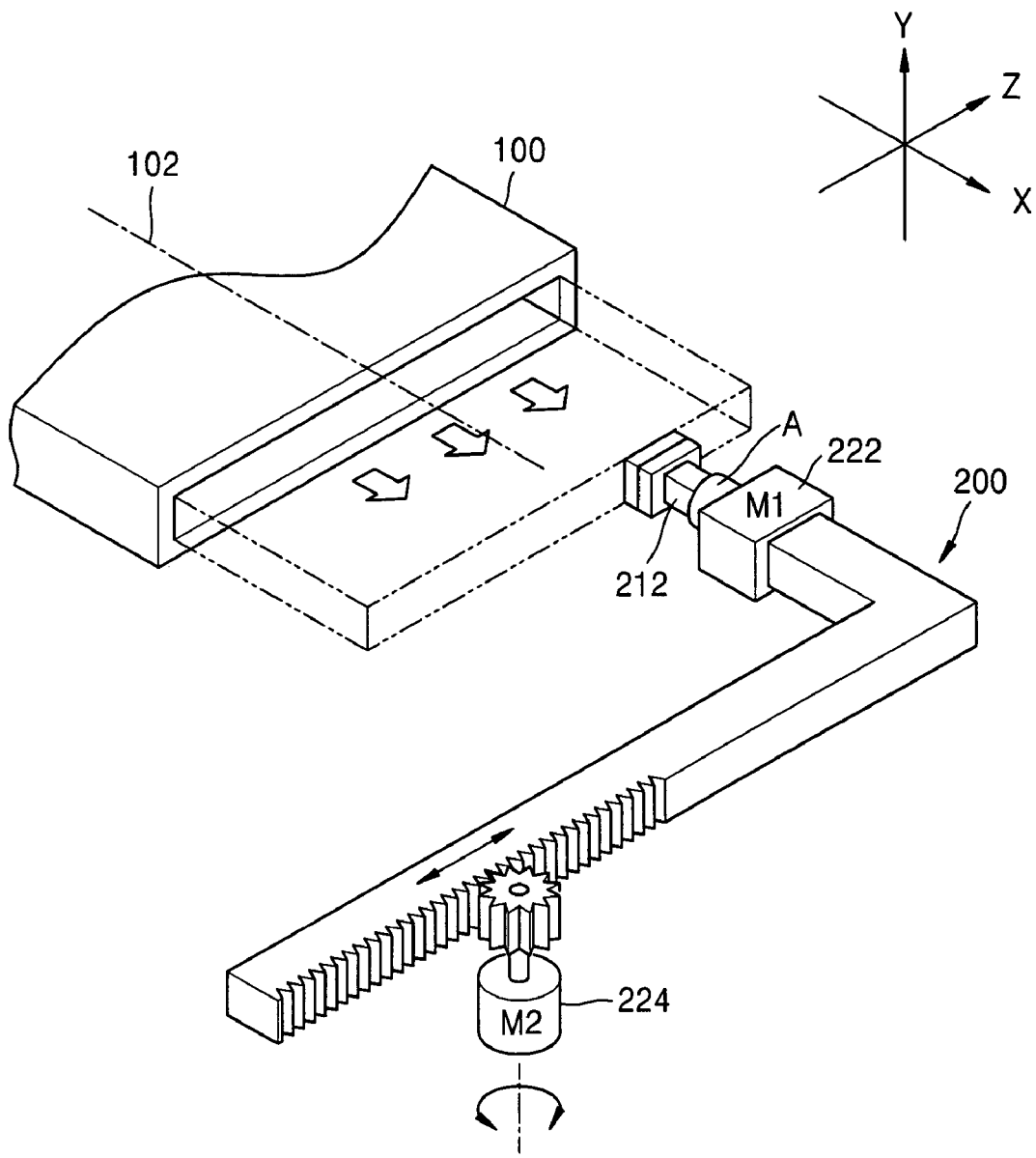
FIG. 1 is a schematic view illustrating an ion beam inclination-angle measuring apparatus for an ion beam according to an embodiment of the present invention.

The attached drawings for illustrating preferred embodiments of the present invention are referred to in order to gain a sufficient understanding of the present invention, the merits thereof, and the objectives accomplished by the implementation of the present invention.

Hereinafter, the present invention will be described in detail by explaining embodiments of the invention with reference to the attached drawings. Like reference numerals in the drawings denote like elements.

Figure 2:
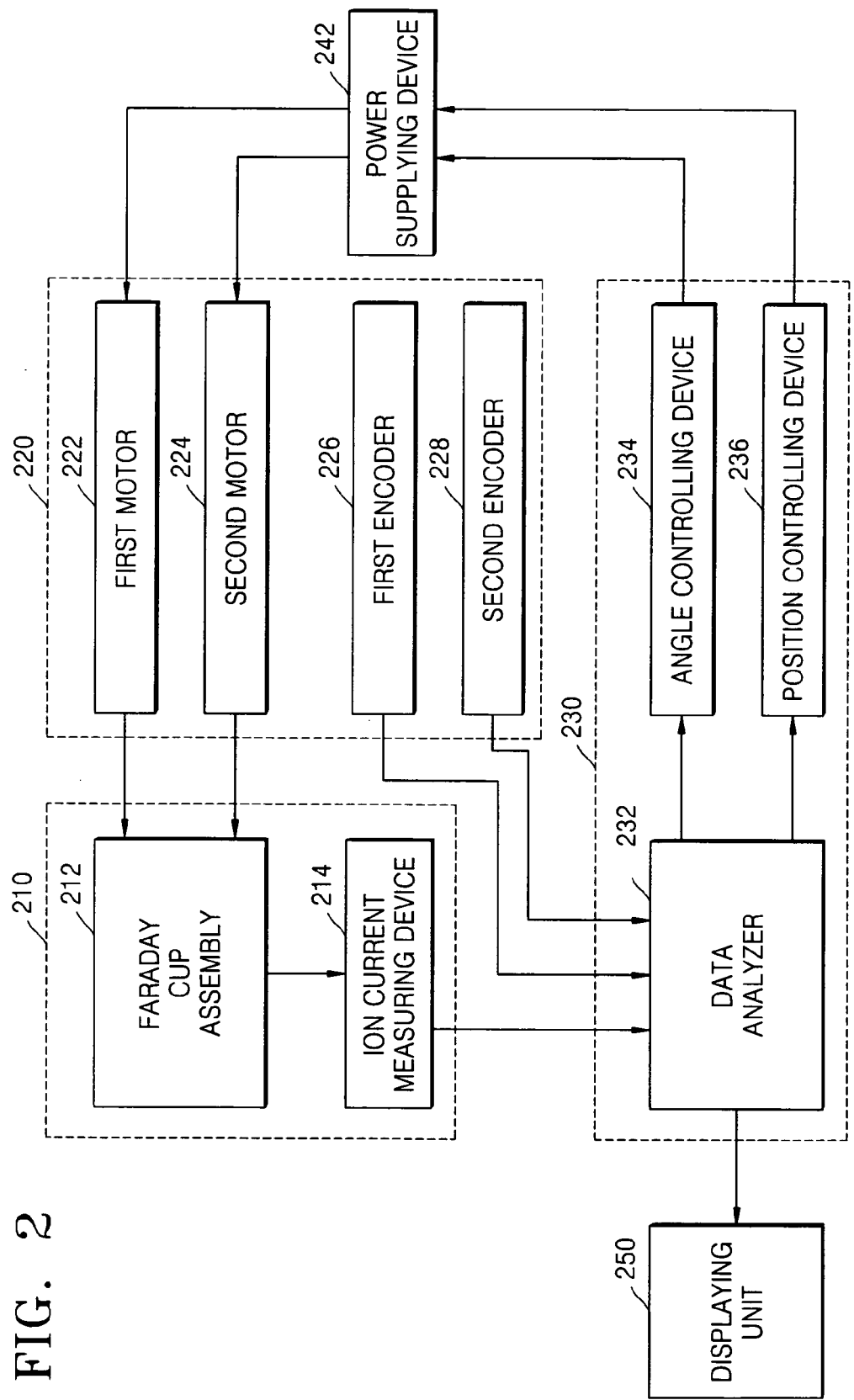
FIG. 2 is a block diagram illustrating the ion beam inclination-angle measuring apparatus of FIG. 1.

FIG. 1 is a schematic view illustrating an ion beam inclination-angle measuring apparatus according to an embodiment of the present invention. FIG. 2 is a block diagram illustrating the ion beam inclination-angle measuring apparatus of FIG. 1.

Referring to FIGS. 1 and 2, the inclination-angle measuring apparatus 200 includes: an ion current measuring unit 210; an angle adjusting unit and position adjusting unit 220; and an inclination-angle calculating unit 230. Additionally, the ion beam received by the inclination-angle measuring apparatus 200 is provided from an ion supplying unit 100. The ion supplying unit 100 forms plasmatic source gas, and extracts a specific ion from the plasmatic source gas to provide an ion beam. FIG. 1 illustrates the ion supply unit 100 for providing a ribbon ion beam having a rectangular section. The ion supply unit 100 is disposed to have a central axis 102 arranged in one direction, for example, in an X-axis direction. Additionally, the ribbon ion beam has a rectangular-shaped vertical section with predetermined length and width being in a Y-axis direction and in a Z-axis direction, respectively.

The ion current measuring unit 210 receives an ion beam from the ion supplying unit 100 and measures an ion current induced by the received ion beam. The ion current measuring unit 210 includes a Faraday cup assembly 212, which is an ion-beam receiving unit, and an ion current measuring unit 214 for measuring ion current induced by the received ion beam.

Figure 3A:
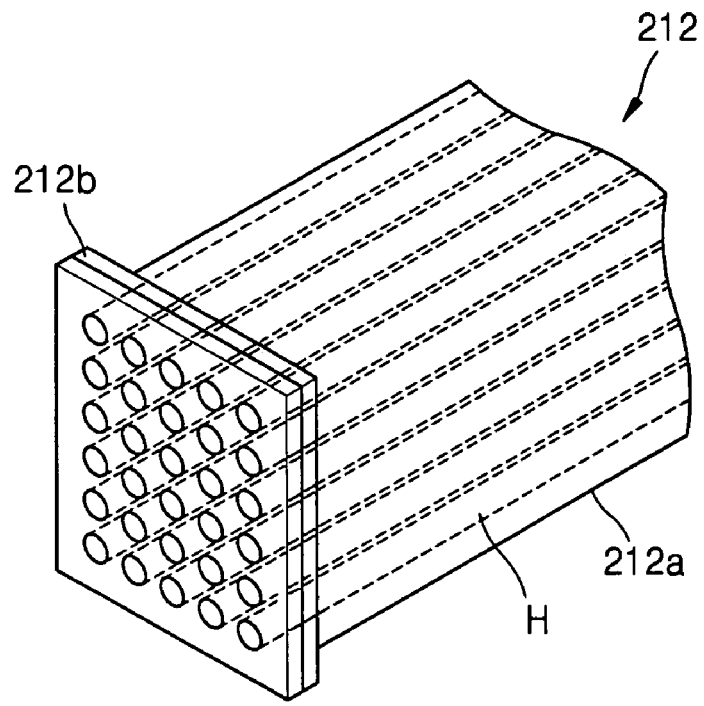
FIG. 3A is an enlarged perspective view illustrating a portion of a Faraday cup assembly according to an embodiment of the present invention.

The Faraday cup assembly 212 is disposed to face the ion supplying unit 100, and receives a portion of the ribbon ion beam from the ion supplying unit 100. FIG. 3A illustrates a schematic perspective view of the Faraday cup assembly 212 according to an embodiment of the present invention.

Referring to FIG. 3A, the Faraday cup assembly 212 includes a Faraday cup body 212a having a plurality of ion-beam receiving holes (H) and a plurality of rings 212b. The Faraday cup body 212a is a unit for directly receiving an ion beam, and is formed of a material having an excellent ion-beam absorptive property such as graphite. The Faraday cup body 212a has a plurality of ion-beam receiving holes (H) arrayed in matrix. Each ion-beam receiving hole (H) can have a circular, rectangular or square section, and preferably may have the circular section.

Each ion-beam receiving hole (H) has a size of 0.1 mm or less. Since each ion-beam receiving hole (H) is provided by punching a rectangular parallelepiped graphite structure, each ion-beam receiving hole (H) has an inlet diameter, which is small, and is uniform irrespective of a depth of the hole.

Figure 3B:
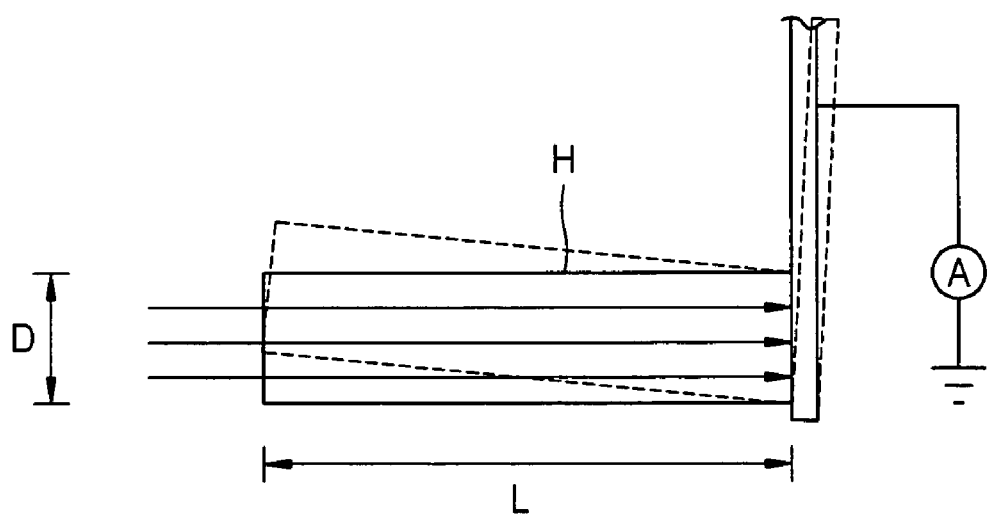
FIG. 3B is a schematic view illustrating a construction of a Faraday cup assembly having a hole for receiving an ion beam according to an embodiment of the present invention.

FIG. 3B is an enlarged perspective view illustrating a portion of the Faraday cup assembly according to an embodiment of the present invention.

Referring to FIG. 3B, the ion-beam receiving hole (H) is small in diameter (D) and has a relatively large length (L). Further, the diameter (D) is unchanged and uniform irrespective of the depth. Therefore, the received ion beam has an excellent detection resolution. Since the ion beam (ion beam absorbed to the Faraday cup body by the ion-beam receiving hole (H) denoted by a dotted line) is not detected at the ion-beam receiving hole (H) which obviates even little at a facing angle, the inclination angle of the ion beam can be measured more precisely. To the contrary, in the case where an ion-beam receiving device that has an ion-beam receiving hole (H) increased in diameter which depends on the increase of its depth, the detection resolution for the ion beam is lower.

Further, the ion-beam receiving hole (H) manufactured in the above described way can be provided with an interval, which is reduced to a minimum, with an adjacent hole (H). Since the ion-beam receiving hole (H) is formed by punching a Faraday cup body, the ion-beam receiving holes (H) can be formed very densely. Accordingly, the present embodiment can prevent a blind region from being generated.

Referring to FIG. 3A, the Faraday cup body 212a has one end having a plurality of rings 212b. The ring 212b of FIG. 3A is exemplarily illustrated. Different structured rings and/or different number of rings may also be provided. The plurality of rings 212b includes a bias ring, an insulating ring and/or a cooling ring. The bias ring prevents secondary electrons from being generated by the ion beam. The insulating ring can be disposed adjacently to the bias ring. Additionally, the cooling ring prevents the temperature from being raised by the ion beam. The plurality of rings 212b can further include an ion cover for absorbing the ion beam, which is not received by the Faraday cup 212a. Detailed functions and the like of the plurality of rings 212b are disclosed in the above-mentioned Keum application.

Referring to FIGS. 1 and 2, the ion current measuring device 214 of the ion current measuring unit 210 is a device for measuring the ion current, which is generated by the ion beam passing through the ion-beam receiving holes (H) of the Faraday cup assembly 212. The ion current can be measured using a current meter connected to the backside of the Faraday cup assembly 212, or can be measured after the ion current is converted into ion voltage in the same manner as the conventional art. In the latter, the ion current measuring device 214 includes a current-voltage converting unit for converting the ion current into the ion voltage, and a voltage measuring device connected with the current-voltage converting unit to measure the converted ion voltage. The measured ion current differs depending on the inclination angle and/or the position of the Faraday cup assembly 212. That is, when the ion-beam receiving hole (H) has a facing direction consistent with the direction of the received ion beam, maximal current flows. The ion beam inclination-angle measuring apparatus 200 measures the inclination of angle of the ion beam by analogizing the inclination angle of the ion beam with the variation of the measured ion current.

The angle and position adjusting unit 220 is a unit for adjusting an angle and/or a position of the Faraday cup assembly 212, and measuring the varied angle and/or position. The angle and position adjusting unit 220 includes a first motor 222 for adjusting an angle of the Faraday cup assembly 212; a second motor 224 for adjusting a position of the Faraday cup assembly 212; a first encoder 226 for measuring the angle of the Faraday cup assembly 212 varied by the first motor 222; and a second encoder 228 for measuring the position of the Faraday cup assembly 212 varied by the second motor 224.

The first motor 222 varies the angle of the Faraday cup assembly 212 about the Y-axis and the Z-axis.

Figure 4:
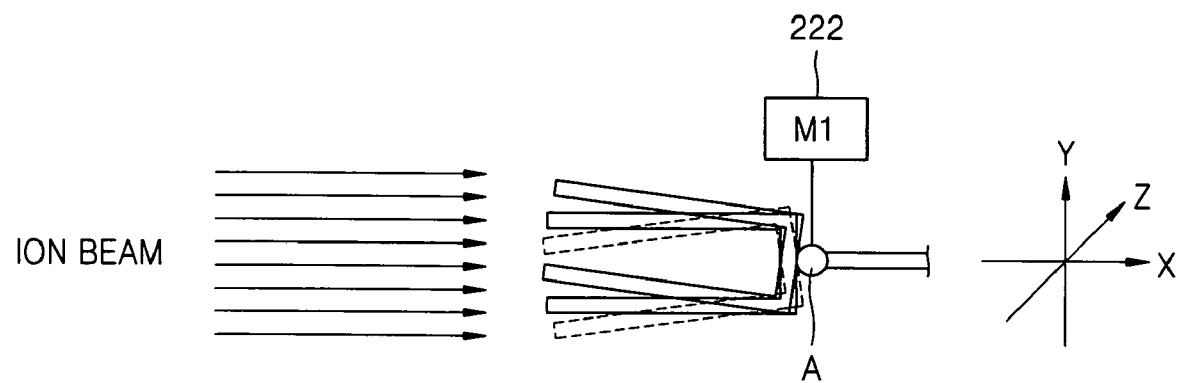
FIG. 4 is a schematic view illustrating an exemplary construction of an angle adjusting unit of a Faraday cup assembly according to an embodiment of the present invention.

FIG. 4 is a schematic view illustrating an exemplary construction of the angle adjusting unit of the Faraday cup assembly 212. Referring to FIG. 4, the Faraday cup assembly 212 freely rotates with respect to a driving shaft (A) provided at the backside thereof centering on the X-axis. That is, if the Faraday cup assembly 212 receives a driving force from the first motor 222 connected with the driving shaft (A), the driving shaft (A) causes the Faraday cup assembly 212 to adjust the angle about the Y-axis and/or Z-axis. The means for adjusting the angle of the Faraday cup assembly 212 is not limited to that of the embodiment of FIG. 4. For example, the angle adjusting unit disclosed in the Keum application can be also used to adjust the angle of the Faraday cup assembly 212.

Additionally, the second motor 224 varies the position of the Faraday cup assembly 212 along the Z-axis. As shown in FIG. 1, a bar (C) connected with the Faraday cup assembly 212 moves in the Z-axis direction by the driving force transmitted from the second motor 224. As a result, the position of the Faraday cup assembly 212 is varied along the Z-axis. Accordingly, even in the case where the Faraday cup assembly 212 is smaller in size than a width of a ribbon ion beam, the inclination angle for an entire ribbon ion beam can be measured. In addition, the inclination angle of a spot ion beam can be also measured. In this case, the second motor 224 does not need to operate. The means for adjusting the position of the Faraday cup assembly 212 is not limited to the illustrated embodiment, and can be modified by those skilled in the art.

Referring to FIGS. 1 and 2, the ion beam inclination-angle measuring apparatus 200 includes an inclination-angle calculating unit 230 for calculating the inclination angle of the ion beam by using information provided from the ion current measuring device 210 and information provided from the angle and position adjusting unit 220. The inclination-angle calculating unit 230 can include a data analyzer 232, an angle controlling device 234, and a position controlling device 236.

The data analyzer 232 receives information on the measured ion current from the ion current measuring device 214. The data analyzer 232 receives, from the first encoder 226, information on an angle at which the Faraday cup assembly 212 is rotated about the Y-axis and Z-axis at the time of receiving information on the ion current. The data analyzer 232 receives, from a second encoder 228, information on the position along the Z-axis of the Faraday cup assembly 212 at the time of receiving information on the ion current. The data analyzer 232 analyzes the ion current information, the rotation angle information and the position information to calculate the inclination angle of the ribbon ion beam at a predetermined position along the Z-axis.

Additionally, the angle controlling device 234 is functionally connected with the data analyzer 232, and supplies power to the second motor 224 through a power supplying unit 242 to drive the second motor 224. Further, the position controlling device 236 is functionally connected with the data analyzer 232 and supplies the power to the first motor 222 through the power supplying device 242 to drive the first motor 222.

The ion beam inclination-angle measuring apparatus 200 can further include a displaying unit 250. The displaying unit 250 is functionally connected with the data analyzer 232, and externally displays information provided from the data analyzer.

Hereinafter, one example of an operation of the ion beam inclination-angle measuring apparatus 200 according to an embodiment of the present invention is described with reference to the attached drawings.

First, the second motor 224 is driven to dispose the Faraday cup assembly 212 at a first position, for example, at one end of the received ribbon ion beam. The second motor 224 is driven to control the power supplying device 242 according to a control signal of the position controlling device 236. The Faraday cup assembly 212 is at an adjusted angle such that its central axis is consistent with a central axis 102 of the ion supplying device 100 at an initial time.

Then, the ion beam is generated from the ion supplying unit 100. The ion beam is received by the Faraday cup assembly 212 through the holes (H) of the Faraday cup assembly 212. An amount of the received ion beam is different depending on the angle of the received ion beam. The ion current detected by the ion current measuring device 214 differs depending on the amount of the received ion beam. Occasionally, any ion current cannot be detected through the ion current measuring device 214. Data on the detected ion current is transmitted to the data analyzer 232.

Continuously, the data analyzer 232 transmits a signal to the angle controlling device 234, and the angle controlling device 234 drives the first motor 222 via the power supplying device 242 on the basis of the received signal. If the first motor 222 is driven, the Faraday cup assembly 212 rotates with respect to the driving shaft (A) about the Y-axis and/or the X-axis. The Faraday cup assembly 212 rotates along a predetermined path previously inputted. The path does not have a specific limitation.

For example, the Faraday cup assembly 212 disposed in parallel with the X-axis can first rotate within a predetermined range at a constant interval about the Z-axis at a fixed angle about the Y-axis, and then second, rotate within a predetermined range at a constant interval about the Y-axis at a fixed angle about the Z-axis. Or, the Faraday cup assembly 212 disposed in parallel with the X-axis can first rotate within a predetermined range at a constant interval about the Y-axis at a fixed angle about the Z-axis direction, and then secondly rotate within a predetermined range at a constant interval about the Z-axis at a fixed angle about the Y-axis direction.

The amount of the ion current detected at the ion current measuring device 214 varies depending on the rotation irrespective of a rotation path of the Faraday cup assembly 212. Information on the amount of the detected ion current is continuously provided to the data analyzer 232. The data analyzer 232 calculates the inclination angle of the ion beam on the basis of the provided information. For example, the data analyzer 232 can calculate the inclination angle of the ion beam from the combination of a Y-axis angle and a Z-axis angle at which the ion current is detected to be at a maximum. At this time, the calculated inclination angle of the ion beam is the inclination angle at a first position of the ribbon ion beam.

After the inclination angle of the ion beam is measured at the first position, the data analyzer 232 transmits the signal to the position controlling device 236. The power supplying device 242 supplies the power to the second motor 224 using the signal to shift the Faraday cup assembly 212 to a second position, for example, at a position shifted by a width of the Faraday cup assembly 212 in the Z-axis from the first position. Additionally, in the same way as at the first position, the Faraday cup assembly 212 is rotated while the ion current is detected to calculate the inclination angle of the ion beam.

This procedure is repetitively performed for the entire ribbon ion beam.

Figure 5:
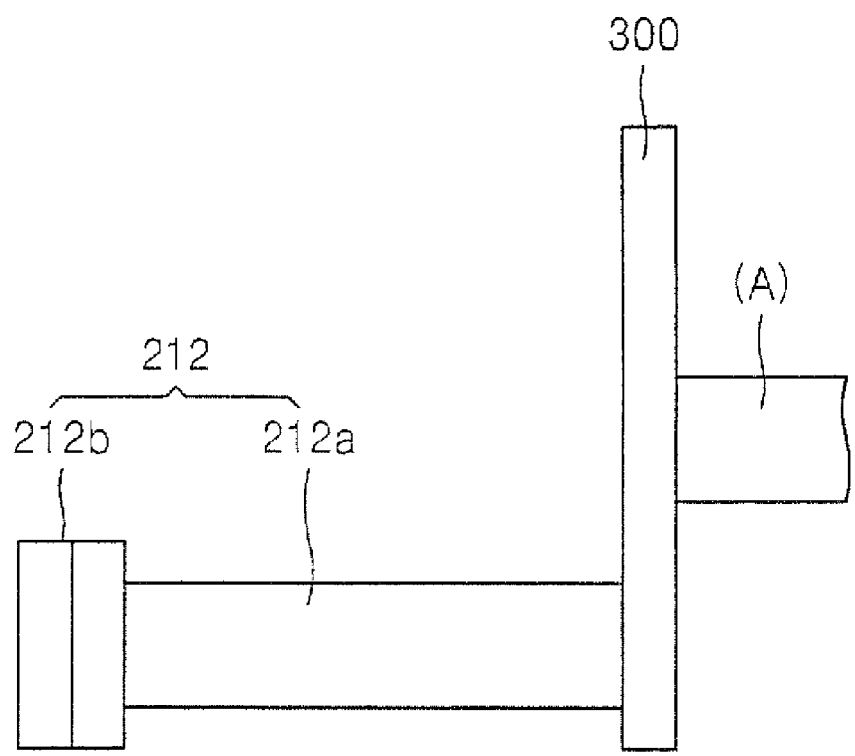
FIG. 5 is a schematic view illustrating an exemplary construction of a Faraday cup assembly installed at a wafer platen of an ion implantation equipment.

Referring to FIG. 5, the Faraday cup assembly 212 may be installed at a wafer platen 300 of an ion implantation equipment. As shown, the Faraday cup body 212a of the Faraday cup assembly is installed at the wafer platen 300.

As described above, since the inclination-angle measuring apparatus shifts a single Faraday cup structure to measure the inclination angle, it can measure the inclination angle of the spot ion beam and the inclination angle of the ribbon ion beam. In addition, the inclination-angle measuring apparatus does not have a blind region, which is represented in a connection region of a plurality of Faraday cup assemblies in the conventional art.

Additionally, since the inclination-angle measuring device for the ribbon ion beam according to the present invention receives the ion beam through a plurality of small-sized holes that are relatively large in length, which measure the inclination angle, the device can measure the inclination angle of the ion beam more precisely.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An ion beam inclination-angle measuring apparatus, comprising:
an ion current measuring unit including an ion-beam receiving device adapted to receive an ion beam in an X-axis direction from an ion supplying unit of an ion implantation device, and including an ion current measuring part adapted to measure an ion current induced by the received ion beam, wherein the ion beam receiving device includes a Faraday cup body having a plurality of holes arrayed in horizontal and vertical directions,
wherein the ion-beam receiving device is installed at a wafer platen of an ion implantation equipment.

2. The apparatus of claim 1, wherein the Faraday cup body is comprised in a single structure.

3. The apparatus of claim 1, wherein each of the plurality of holes has a diameter in the range from about five micrometers to less than 1 millimeter.

4. The apparatus of claim 1, wherein each of the plurality of holes has a circular, rectangular or square cross-section.

5. The apparatus of claim 1, wherein a material of the Faraday cup body exists contiguously between sidewalls of adjacent ones of the plurality of holes.

6. The apparatus of claim 5, wherein the material comprises graphite.

7. The apparatus of claim 1, wherein a length of each of the plurality of holes is greater than a diameter of each of the plurality of holes.

8. The apparatus of claim 1, wherein the Faraday cup body comprises a rectangular parallelepiped structure and wherein each of the plurality of holes is formed by punching the rectangular parallelepiped structure.

9. A method of measuring an inclination-angle of a ribbon ion beam, comprising:
providing a ribbon ion beam in an X-axis direction from an ion supplying unit of an ion implantation device;
measuring an inclination angle of a first portion of the ribbon ion beam; and
after measuring the inclination angle of the first portion of the ribbon ion beam, measuring an inclination angle of a remaining portion of the ribbon ion beam.

10. The method of claim 9, wherein measuring an inclination angle of the remaining portion of the ribbon ion beam includes repetitively measuring the inclination angle of the remaining portion of the ribbon ion beam.

11. The method of claim 9, wherein measuring the inclination angle of the first portion of the ribbon ion beam and measuring the inclination angle of the remaining portion of the ribbon ion beam are performed by a movable ion beam inclination-angle measuring apparatus comprising:
an ion current measuring unit including an ion-beam receiving device adapted to receive an ion beam in an X-axis direction from an ion supplying unit of an ion implantation device and including an ion current measuring part adapted to measure an ion current induced by the received ion beam, wherein the ion beam receiving device includes a Faraday cup body having a plurality of holes arrayed in horizontal and vertical directions.

12. A method of measuring an inclination-angle of an ion beam, comprising:
providing ribbon ion beam in an X-axis direction from an ion supplying unit of an ion implantation device;
disposing an ion-beam receiving device including a central axis parallel with the X-axis, the ion-beam receiving device including a Faraday cup body having a plurality of holes arrayed in horizontal and vertical directions;
moving the ion-beam receiving device in the Z-axis direction by a predetermined interval;

measuring an ion current induced by a portion of the ribbon ion beam at each interval while rotating the central axis of the ion-beam receiving device about a Y-axis and/or an Z-axis; and calculating an inclination angle of the portion of the ribbon ion beam at each interval from the measured ion current.

13. The method of claim 12, wherein calculating an inclination of another portion of the ribbon ion beam is repeated until an inclination angle of the entirety of the ion beam is calculated.

* * * * *